United States Patent
Yazigi et al.

(10) Patent No.: US 7,695,280 B1
(45) Date of Patent: Apr. 13, 2010

(54) DENTAL IMPLANT AND DRILL FOR FORMING SOCKET FOR THE SAME

(76) Inventors: Ernest M. Yazigi, 1 Longfellow Pl., #1621, Boston, MA (US) 02114; Anas M. Shaar, 325 Union St., Braintree, MA (US) 02184

(*) Notice: Subject to any disclaimer, the term of this patent is extended or adjusted under 35 U.S.C. 154(b) by 587 days.

(21) Appl. No.: 11/305,250

(22) Filed: Dec. 16, 2005

(51) Int. Cl.
*A61C 3/02* (2006.01)

(52) U.S. Cl. .................................... 433/165

(58) Field of Classification Search ............ 433/165, 433/166; 408/199–233; 81/57.22, 57.29, 81/57.28, 57.13, 57.12, 57.26, 57.31, 57.46; 175/327–435; 409/143
See application file for complete search history.

(56) References Cited

U.S. PATENT DOCUMENTS

| | | | |
|---|---|---|---|
| 513,088 A * | 1/1894 | Crane | 408/53 |
| 1,297,740 A * | 3/1919 | Schimdgall | 408/25 |
| 1,641,031 A | 8/1927 | Gaillard | |
| 1,669,423 A * | 5/1928 | Schmidgall | 408/25 |
| 2,449,522 A | 9/1948 | White | |
| 2,542,695 A | 2/1951 | Neff et al. | |
| 4,175,324 A | 11/1979 | Arai | |
| 4,197,645 A * | 4/1980 | Scheicher | 433/128 |
| 4,353,698 A | 10/1982 | McSpadden | |
| 4,571,183 A | 2/1986 | Nash | |
| 4,682,660 A * | 7/1987 | Barthelemy et al. | 175/96 |
| 4,787,848 A | 11/1988 | Ross | |
| 5,000,628 A * | 3/1991 | Sandoval | 408/25 |
| 5,085,543 A * | 2/1992 | Click | 408/48 |
| 5,246,370 A | 9/1993 | Coatoam | |
| 5,785,525 A | 7/1998 | Weissman | |
| 5,944,526 A | 8/1999 | Liu | |
| 5,947,730 A | 9/1999 | Kaldestad | |
| 6,039,568 A | 3/2000 | Hinds | |
| 6,171,312 B1 | 1/2001 | Beaty | |
| 6,213,774 B1 | 4/2001 | Lazarof | |
| 6,428,317 B1 | 8/2002 | Abel | |
| 6,672,872 B2 | 1/2004 | Cottrell | |
| 7,059,812 B2 * | 6/2006 | McFarlane | 408/53 |
| 2002/0039718 A1 | 4/2002 | Kwan | |

OTHER PUBLICATIONS

"Biaxial Implant Positioning" Pamphlet, Southwest Center for Dentistry, Feb. 16, 2005.

* cited by examiner

*Primary Examiner*—Cris L Rodriguez
*Assistant Examiner*—Sunil K Singh
(74) *Attorney, Agent, or Firm*—Cesari and McKenna, LLP; Michael R. Reinemann

(57) ABSTRACT

A drill forms a dental implant fixture socket having an ovular cross section with a series of tapering tiers that are widest near the gumline and narrowest near the root. The drill may have laterally oriented opposed drill points each having an ovoid or conical shape. Mechanical transmission elements operatively connect the gears to a dental hand piece. A plurality of differently sized drill point pairs can be provided along the length of a framework to allow a multi-tiered socket to be formed in a single drilling pass. An implant fixture may have a generally ovular or non-circular cross section having a plurality of tiers that successively narrow in a direction from the gumline region toward root region. The tiers are adapted to fit snugly with the resulting socket tiers formed by the drill. The fixture can be adapted to receive abutments.

17 Claims, 10 Drawing Sheets

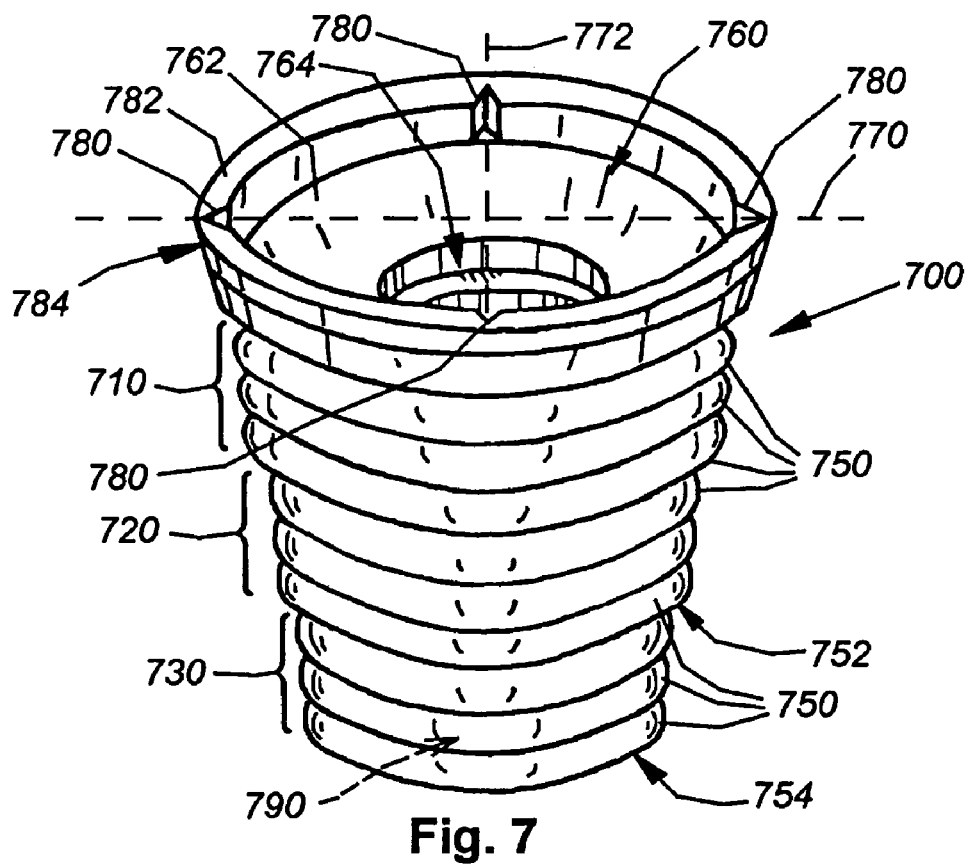
Fig. 7
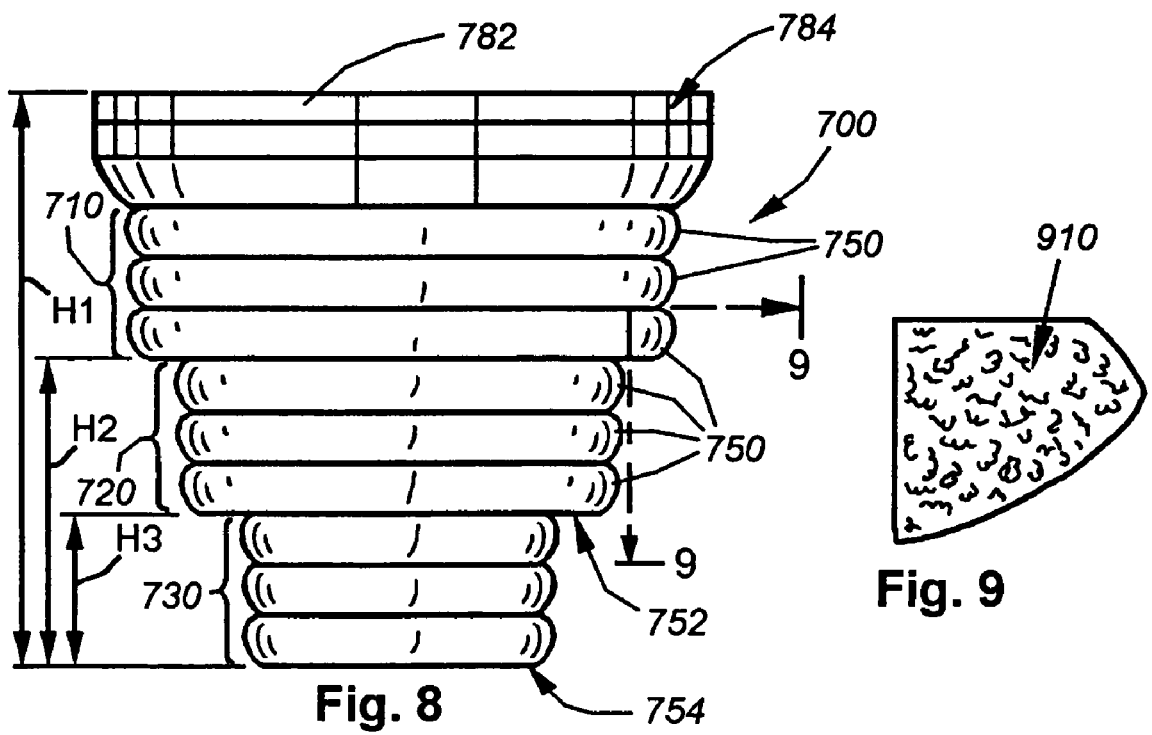
Fig. 8
Fig. 9

DENTAL IMPLANT AND DRILL FOR FORMING SOCKET FOR THE SAME

BACKGROUND OF THE INVENTION

1. Field of the Invention

This invention relates to dental implants and drills for forming sockets for receiving the anchor section of such dental implants.

2. Background Information

Dental implants have been employed for generations to replace lost and damaged teeth. In general, most modern dental implants consist of a fixture that is screwed or press-fit into a socket that has been drilled or carved into the patient's jawbone. The size of the fixture varies in accordance with the location and anatomy of the mouth. The fixture is held in place by friction or adhesive. Many modern implant fixtures include a surface having a generalized texture and/or ridged surface. This allows for eventual osseointegration—that is, the patient's bone grows into and around the fixture to more permanently secure it to the jawbone.

The fixture may include a cylindrical or conical abutment that projects upwardly from the socket to provide a mounting point for an artificial crown or bridge. Such an abutment may be integral with the fixture, or more commonly, is separately attached to the implant fixture using fasteners, such as screws. The implant fixture may have a polygonal socket with a threaded bottom that ensures proper rotational orientation for the inserted abutment and, hence, proper orientation for the crown or bridge that is seated on the abutment. The crown or bridge simulates the actual tooth or teeth being replaced. The crown or bridge can be attached to the abutment by a variety of techniques including adhesives.

A common disadvantage of current implants is that the socket formed in the fixture is either too small in diameter (in the case of a drilled and threaded fixture) or too large in diameter (in many press-fit fixtures). In general, natural tooth sockets in the jawbone tend to be ovular, and a round hole either underfills or overfills this area. Thus, where the diameter is too small, the fixture may not fully fill the original tooth socket and/or may not be firmly attached. Conversely, the circular hole that must be drilled in the jawbone (in the tooth socket) to accommodate a larger, round cross-section fixture may cause the walls of the jawbone to be overly thinned in places, leading to possible failure of the bone. U.S. Pat. No. 5,785,525, entitled DENTAL IMPLANT SYSTEM, by Weissman contemplates the formation of implants having a non-round cross section. A non-circular shape better conforms to the actual shape of a socket of the tooth. However, forming a non-circular hole having a depth and size that accurately reflects the volume and desired of the implant is quite difficult. In general, non-circular holes are formed using a broaching technique, in which a linear drill is driven using hammer blows into the jawbone. The possibility of overdrilling and/or fracture is always present in this technique. In addition, Weissman creates straight non-circular holes without a varying cross section along their lengths. A natural socket is tapered inwardly from the gumline to the root. By removing a large quantity of material near the root, the risk of infection and weakening of the jawbone is increased.

It is, thus, desirable to provide a system and method for forming a receiving socket for a dental implant that avoids the disadvantages of the prior art. A drill that more easily and accurately creates such a socket is desirable and the implant fixture received by the socket should more naturally conform to the contours of the original tooth socket. Also, it is desirable to provide a system that allows for immediate replacement of the tooth following tooth extraction.

SUMMARY OF THE INVENTION

This invention overcomes the disadvantages of the prior art by providing a drill for forming a dental implant fixture socket that has an ovular cross section with a series of tapering tiers that are widest near the gumline and narrowest near the root. The drill comprises one or more pairs of laterally (transverse to the downward-drilling direction) oriented opposed drill points each having a half-ovoid or conical shape, although a variety of shapes can be employed. More particularly, each drill point in a pair tapers in an opposite direction with respect to the other drill point, with both rotating upon an axle operatively connected to a central drive gear within a narrow central framework. The axle is oriented perpendicular to the downward drilling direction. By changing the direction of the drilling axis from vertical rotation to horizontal rotation allows the creation of anatomical oval shape drill hole/socket aligned appropriately in buccal-lingual and mesial-distal directions. The framework includes a bottom stop that sets the downward limit and guides the travel of the drill into a predrilled pilot hole. A series of gears or other mechanical transmission elements operatively connects the drive gear to a dental hand piece. A plurality of differently sized drill point pairs can be provided along the length of the framework to allow a multi-tiered socket to be formed in a single drilling pass. The pairs are connected via gears or other transmission elements. The points can is be adapted to counter-rotate with respect to adjacent pairs to assist in discharging material.

An implant fixture for insertion into the socket formed by the drill can comprise a generally ovular or non-circular cross section having a plurality of tiers that successively narrow in a direction from the gumline region toward root region. The tiers are adapted to fit snugly with the resulting socket tiers formed by the drill. The implant is adapted to press fit into the formed socket. The implant fixture can include a textured surface for bone growth thereinto and a polished ring near the gumline. The fixture can be adapted to receive abutments using fasteners or other attachment systems. Each tier of the fixture can include a series of separate, parallel ringlets to aid in forming a secure fit.

The drill and implant fixture of this invention make possible the immediate placement of an implant following tooth extraction.

BRIEF DESCRIPTION OF THE DRAWINGS

The invention description below refers to the accompanying drawings, of which:

FIG. 7 is a top perspective view of a dental implant fixture for insertion into a socket formed by the drill according to the illustrative embodiment;

FIG. 8 is a side view of the implant of FIG. 7;

FIG. 9 is a more-detailed close-up of an exemplary surface texture applied to the implant taken along section lines 9-9 of FIG. 8;

DETAILED DESCRIPTION OF AN ILLUSTRATIVE EMBODIMENT

Figure 1:
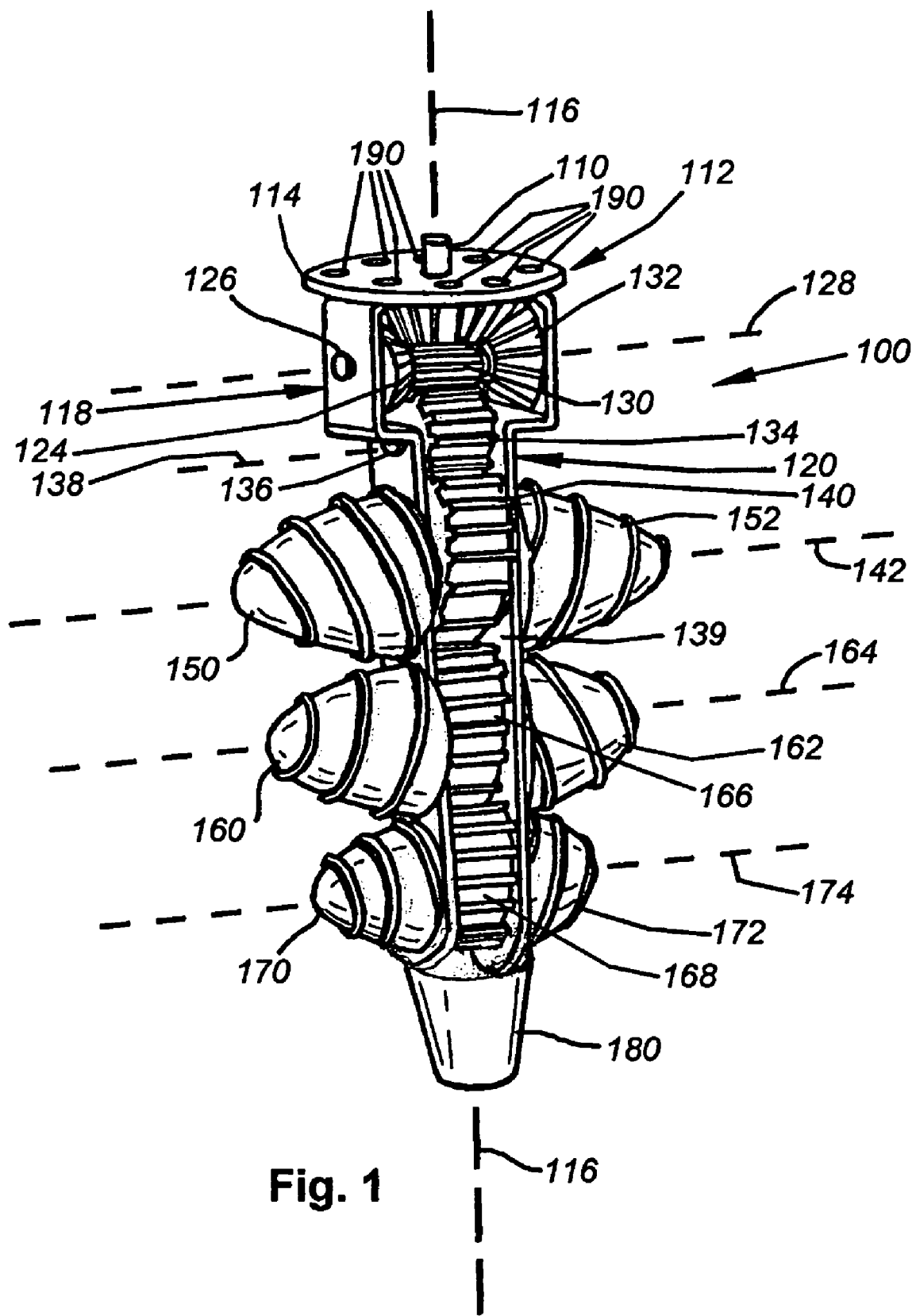
FIG. 1 is a perspective view of a multi-point drill that forms a socket for receiving a dental implant fixture in accordance with an illustrative embodiment of this invention.
Figure 2:
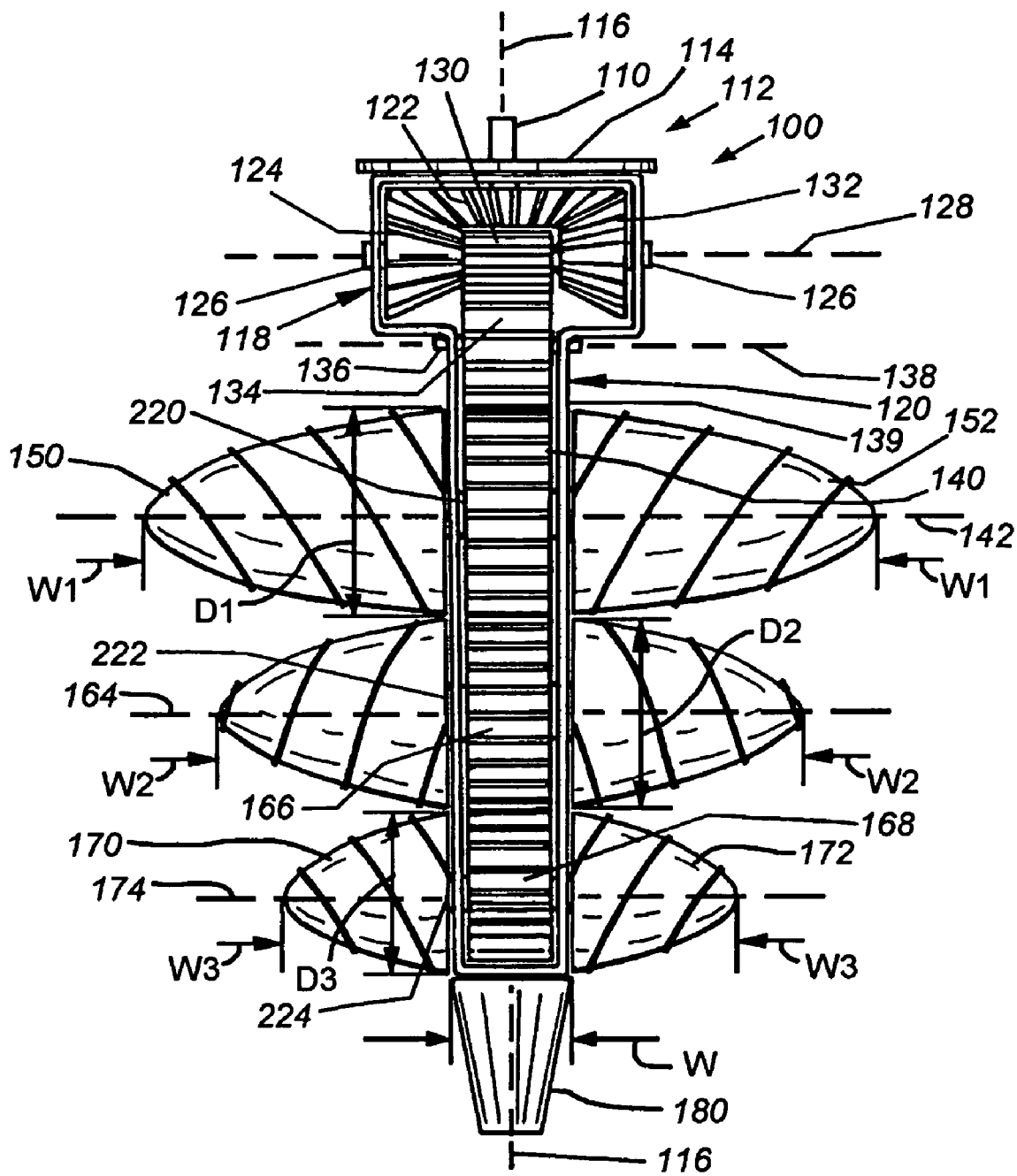
FIG. 2 is a side view of the drill of FIG. 1.

FIGS. 1 and 2 detail a drill assembly 100 that forms a novel socket shape in a jawbone for receiving a dental implant fixture in accordance with an embodiment of this invention. The drill assembly 100 includes a main drive shaft 110 located at a top end 112 of the drill assembly 100. The drive shaft is adapted to engage the chuck of a conventional or customized dental hand piece (see below). An indexing fixture 114 is provided. This allows the drill assembly to be secured against rotation about the vertical (downward drilling direction) axis 116, about which the drive shaft 110 rotates. The drive shaft 110 passes into an upper portion 118 of a drill framework 120.

The upper portion includes a main bevel gear 122 that rotates about the vertical axis 116. This gear is fixed to the shaft 110. Note that appropriate bearings can be provided to this and other rotating components described herein to facilitate low-friction, low-wobble operation. The main bevel gear engages a lateral bevel gear 124 mounted on a lateral axle 126 that passes through, and is supported by, the sides of the framework upper portion 118. The lateral axle 126 is oriented along a first transverse axis 128 that is perpendicular with respect to the vertical (downward drilling direction) axis 116. The lateral bevel gear is fixedly attached to a first straight cylindrical gear 130 that is located on the axle 126. Thus, when the lateral bevel gear 124 rotates, it rotates the straight gear 130. An idling bevel gear 132 is provided on the side opposite the lateral bevel gear. This idling gear rotates freely with respect to the lateral bevel gear 124 and straight gear 130. In this manner, the idling gear 132 provides force balance to the gear train as it rotates contra to the lateral bevel gear 124 and straight gear 130. In alternate embodiments, the idling bevel gear can be omitted.

The straight gear 130 transmits rotation to an intermediate or second straight gear 134 mounted on an axle 136 centered on a second lateral axis 138 below the first lateral axis 128. The diameter of the first straight gear 130 and diameter of the second straight gear 134 collectively determine the rotational speed of each drill point in the assembly, as described generally below. The second straight gear 134 passes in a space between the enlarged enclosure of the framework upper portion 118 into the narrowed drill section 139 of the framework. The second straight gear 134 interconnects with a third straight gear 140 that is fixedly attached to an upper set of laterally opposed drill points 150 and 152 via an axle 220 that passes between the third straight gear 140 and each of the drill points. These points 150, 152 and the gear 140 all rotate on a third lateral axis 142. Note that the drill points herein are constructed from an acceptable material with an appropriate cutting surface. In this embodiment, the points all have conventional spiral cutting teeth (oriented in the proper direction for rotation) and are formed from hardened steel alloy. However, use of various surface textures and materials (tungsten carbide, diamond, etc.) is expressly contemplated according to alternate embodiments. Each of the points has a conical or half-ovoid shape as shown. The resulting socket formed by this shape is described further below.

A center set of drill points 160 and 162 rotates on an axle 222 about a fourth lateral axis 164. The axle 222 passes through the framework and is fixedly attached to each point 160, 162 and to a fourth straight gear 166. Rotation is transmitted from the third straight gear to the fourth straight gear, and thus, to the center drill points 160, 162.

A fifth straight gear 168 is mounted in engagement with the fourth straight gear 166. This gear is fixedly attached to the axle 224 that passes through the framework and is fixedly attached to the lower set of drill points 170, 172. This set and gear rotate about the fifth lateral axis 174.

Each set of points 150 and 152, 160 and 162, 170 and 172, respectively, is successively smaller in width W1, W2, W3 and Maximum diameter D1, D2, D3. The respective straight gear 140, 166 and 168 has an average (meshing) diameter that is slightly larger that the maximum point diameter. Thus, the points are closely spaced along the vertical axis 116, but do not touch.

As will be discussed further below, the drill section 139 of the framework is sized so that it is no wider than the maximum diameter (D1, D2, and D3) of the adjacent drill points. Similarly, the maximum lateral width W (FIG. 2) of the drill section 139 between straight gears is made as narrow as practicable in this embodiment.

The bottommost tip of the drill section 139 includes a pilot tip 180 aligned with the vertical axis 116. The tip has a diameter approximately the same as, or slightly smaller than the width W. The tip has a length that is set based upon the desired distance between the lower drill points 170, 172 and bottom of a pilot hole (described below). The tip 180 can have a variety of shapes including be cylindrical, or frustoconical (tapered) as shown. While the illustrative embodiment shows an exposed gear train, any part, or all, of the framework can be enclosed and appropriate seals can be provided to maintain isolation between gears and the outside environment.

Having described the general structure of the drill assembly 100 in accordance with an illustrative embodiment, reference is now made to FIGS. 3-6, which outline the steps undertaken in employing the drill assembly to form a socket for receiving a dental implant in accordance with this invention. In general, by changing the direction of the drilling axis from vertical rotation to horizontal rotation allows the creation of anatomical oval shape drill hole/socket aligned appropriately in buccal-lingual and mesial-distal directions.

Figure 3:
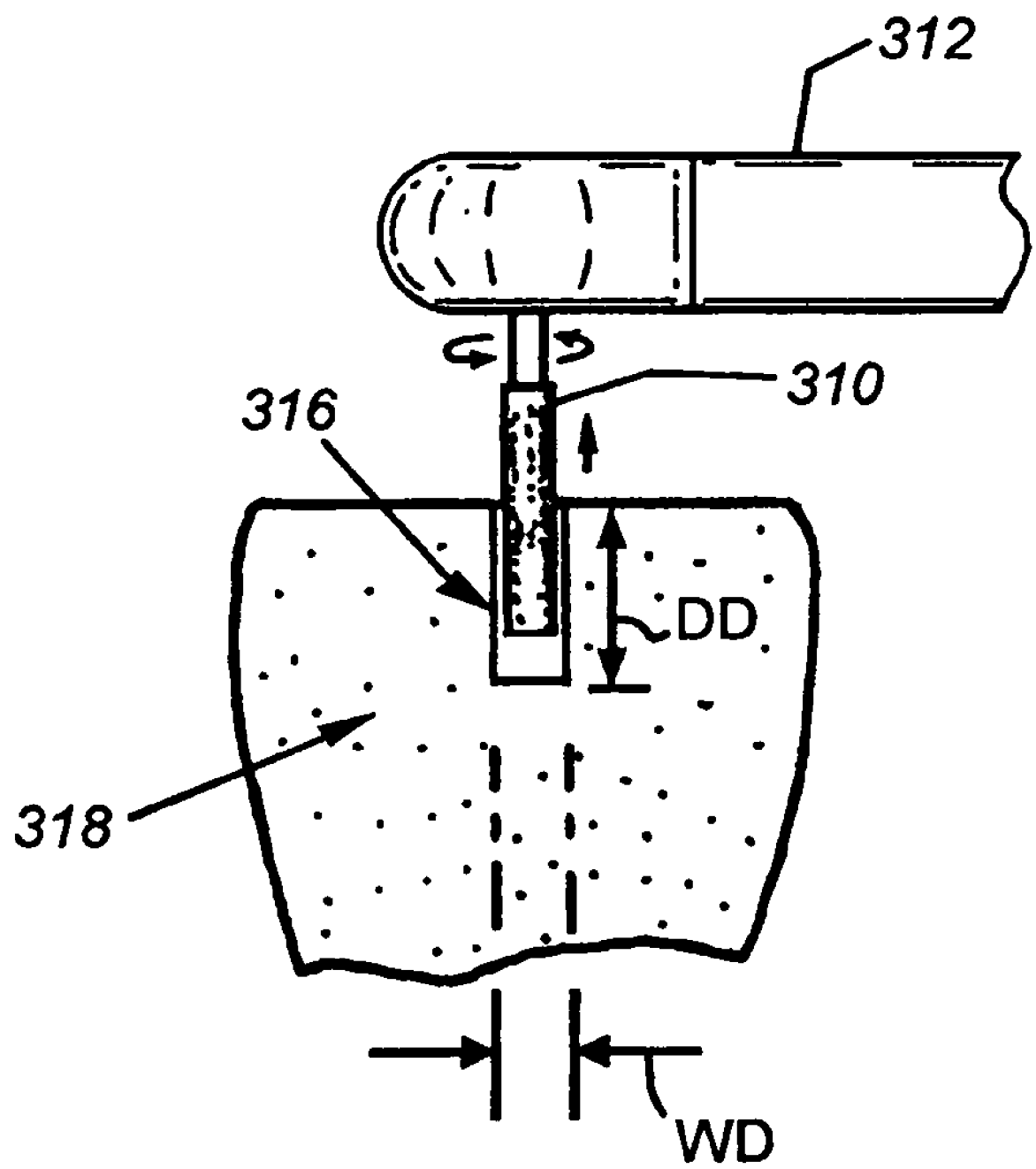
FIG. 3 is a partial side cross section showing the creation of a pilot hole in jawbone material for receiving the drill in accordance with the illustrative embodiment.

FIG. 3 shows an initial step in which a conventional cylindrical drill bit 310, mounted on a dental drill hand piece 312 forms a hole 316 in a jawbone. The surrounding material of the socket is omitted for clarity. The drill is allowed to form a hole having a maximum depth DD and diameter WD that is appropriate to the size and shape of the tooth being replaced. The diameter WD of the pilot hole is approximately 2 mm-3 mm in this embodiment. It can be formed by a single drill pass of by stepping-up in size from a smaller sized to a larger sized drill. Note that various pilot hole diameters are expressly contemplated. The angle and depth of the pilot hole determines the final size, depth and placement of the socket and implant. Thus, care is taken in this first step to creation of an accurate pilot hole.

Figure 4:
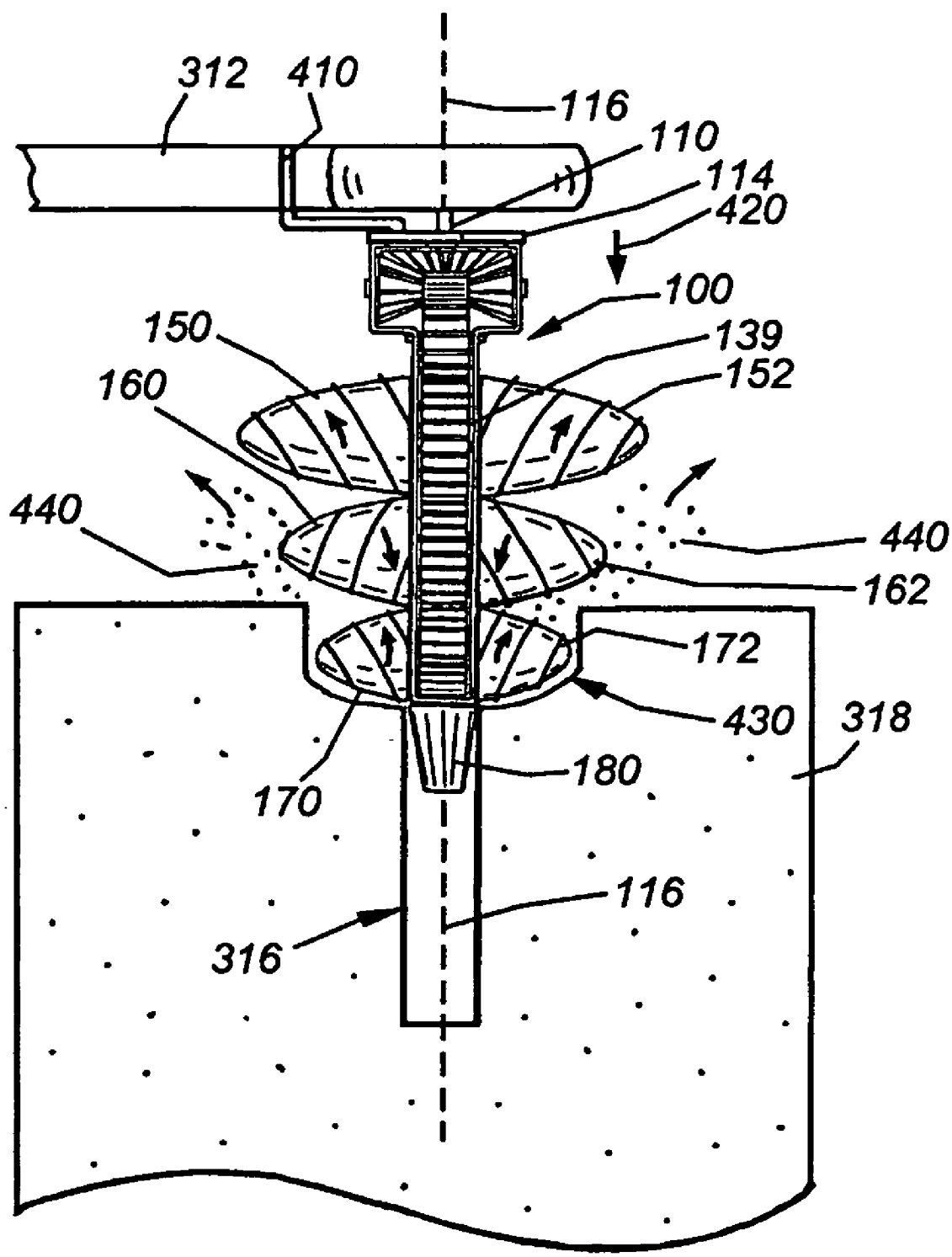
FIG. 4 is a partial side cross section showing the action of the drill in accordance with the illustrative embodiment as the bottom tier of drill points engages the jawbone to material.

After completing the pilot hole 316, the pilot drill 310 is removed from the jawbone 318, and the drill assembly 100 is attached to the hand piece 312. A separate hand piece/adapter can be employed where appropriate. The hand piece includes an integral or retro-fitted (as shown in FIG. 4) locking pin assembly 410 that removably engages at least one of the holes 190 (FIG. 1) provided on the top of the indexing head 114. When the to shaft 110 is chucked in the hand piece 312, the locking pin assembly 410 prevents rotation of the assembly about the vertical axis 116, so that all rotational motion is transmitted exclusively to the assembly's gear train. Thus, as shown, the tip 180 passes into the pilot hole and the lowest set of drill points 170, 172, rotating laterally, dig out the adjacent material. The width of the drill section 139 of the framework 139, being small enough passes into the pilot hole as the points 170, 172 descend (arrow 420).

Referring further to FIG. 4, the tip 180 is guided into the pilot hole to cause the lowest tier of lateral drill points 170, 172 to bore an ovular hole 430. The opposing elongated ends of the oval (major axis) are defined by the curvature and size of the opposing drill points, while the maximum minor axis is generally defined by the pilot hole. In this embodiment, the pilot hole is a single diameter along its length (a straight cylinder). If a large-diameter pilot hole is employed, then the maximum minor axis will be approximately the same for each tier of drill points (e.g. the minor axis is the diameter of the pilot hole). The pilot hole can be a tapered or stepped hole in alternate embodiments so that the minor axis more smoothly transitions into the opposing half-ovals formed by the drill points. By maintaining a small pilot hole diameter (smaller than the maximum diameter D1, D2, D3 of the drill points) and relatively small-width framework drill section (139), the size of the central pilot hole will not affect overall ovular socket shape is minimized. This assumes that the two opposing drill points dig out material greater in area than the original pilot hole. Any bone material in small gap between the opposing ends of the drill points that is taken up by the framework is simply broken away as the drill points bore into the material.

As shown, the points 170, 172 create a stream of ejected material 440 that is driven out of the socket by rotation of the points combined with their spiral cutting head shape.

Figure 5:
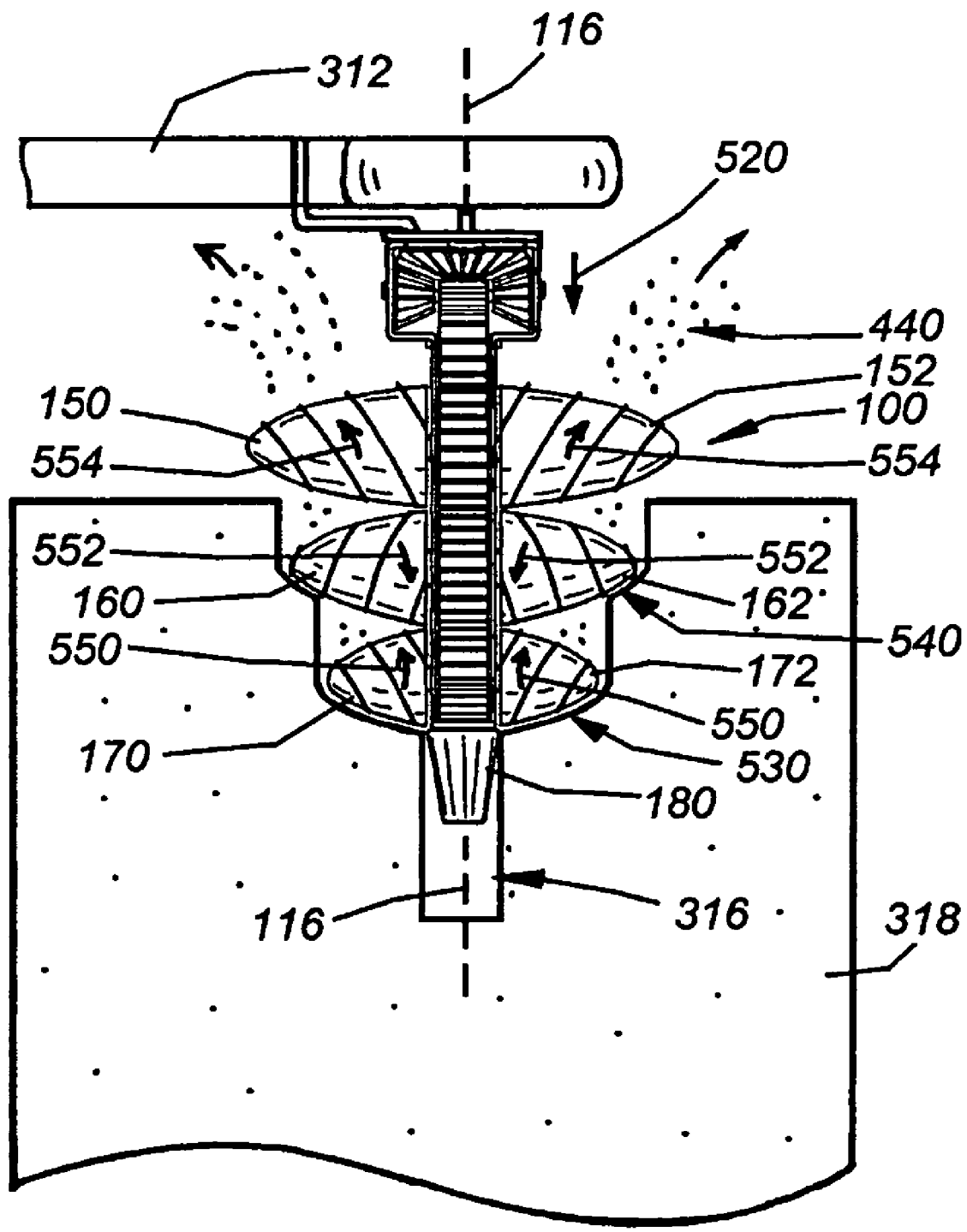
FIG. 5 is a partial side cross section showing the action of the drill in accordance with the illustrative embodiment as the central and bottom tiers of drill points engage the jawbone material.

Referring to FIG. 5, the drill assembly 100 continues its downward travel (arrow 520) into the socket. The lowest tier of drill points 170, 172 continue to form the smallest ovular hole 530, while the central tier of points 160, 162 have now entered the socket and are digging out further material behind that already removed by the lowest points 170, 172. This forms the next-largest ovular hole 540, above the smallest/ lowest ovular hole 530. Notably, the next largest set of points is presented with somewhat less material to remove as the lower set has already removed part of the total material. The arrangement of gears naturally causes each set of drill points to counter rotate (arrows 550, 552 and 554) with respect to adjacent sets. This counter-rotation further assists in the transportation of ejected material 440 out of the socket, which also aids in collecting bone for grafting.

Figure 6:
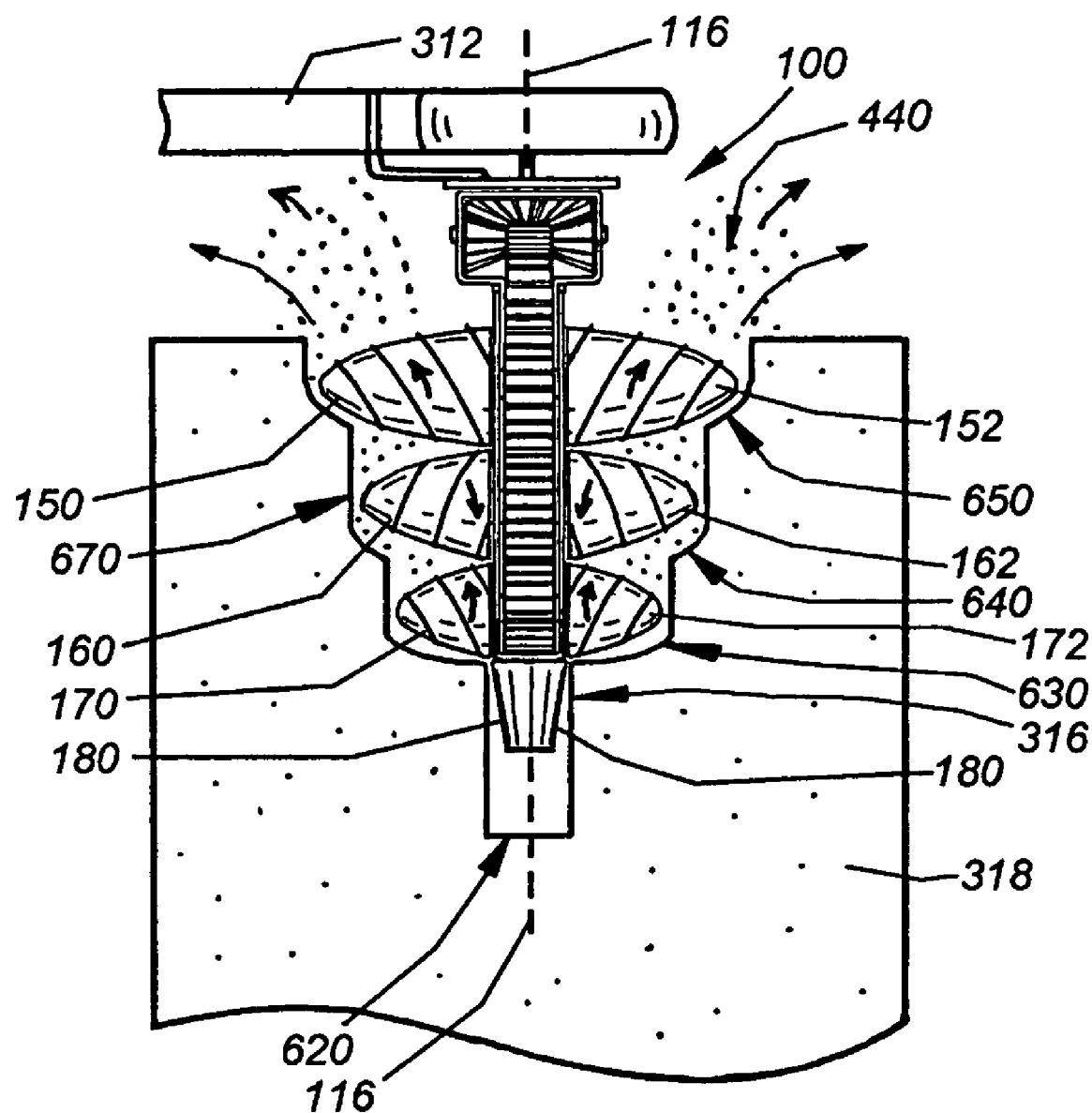
FIG. 6 is a partial side cross section showing the action of the drill in accordance with the illustrative embodiment as a the upper, central and bottom tiers of drill points engage the jawbone material.

Finally, in FIG. 6 the drill assembly 100 has reached its bottom limit with the tip 180 contacting the bottom 620 of the pilot hole 316. The relation of the pilot hole depth to the tip, thus, sets the position and depth of the completed socket. In this embodiment, the upper tier of drill points 150, 152 has now created the largest ovular hole 650 above the smaller central ovular hole 640 and the lowest ovular hole 630—both of which smaller holes have been formed to full depth by the completed progress of the of the central and lowest tiers of drill points, respectively. The resulting socket 670 is now ready to receive an appropriate implant fixture in accordance with the illustrative embodiment.

The implant fixture 700 is shown in further detail in FIGS. 7-10. The implant is constructed from a biocompatible material having suitable strength and durability. In one embodiment, titanium metal is employed. Ceramics and/or other materials can be used in alternate embodiments for all or part of the implant 700. The implant in this embodiment is constructed in the form of an oval (see FIG. 10) with at least three distinct tiered sections 710, 720 and 740 along its vertical length. The tiered sections of the implant 700 define a general outside dimension that conforms in shape and size to the dimensions of the finished socket 670 (FIG. 6) formed by the drill assembly 100 of the illustrative embodiment. Within each tiered section, a set of annular rings 750 are defined. These rings are optional, but are provided to afford further irregularities in the surface for bone growth and/or press-fitment to occur. Optionally, the lowest ring (752, for example) of each tier (720, for example) includes a rounded-over transition into the next-lowest tier (or bottom 754) that conforms generally to the shape formed by the drill point at this location. While annular rings 750 are employed as a further holding mechanism, a variety of differing surface shapes and/or irregularities (or a smooth surface) can be employed to assist ion securing the implant 700 into the socket.

The implant also includes an open top end 760 for receiving an abutment (described further below). The top end includes an enlarged frustoconical well and a central threaded hole for receiving a fastener that secures the abutment into the implant 700. Four evenly spaced (at the major axis 770 and minor axis 772) registration notches in the lip 782 of the well 762 engage corresponding wedge projections (see below) on the abutment to prevent rotation and/or movement of the abutment relative to the implant. The lip 782 includes a polished outer surface 784 formed (unitarily) from the same material as the rest of the implant 700, or applied to the implant. Polished and non-polished surface can be used for the lip. When the polished surface is used, the polished surface reduces the chance of irritation and infection at the gumline and provides better gum attachment and/or shaping. Conversely, as detailed in FIG. 9, the remaining implant surface (or portions thereof) includes a sintered, roughened or otherwise finely textured surface 910 that aids in the growth of jawbone material thereinto to permanently anchor the implant into the jawbone over time.

Figure 10:
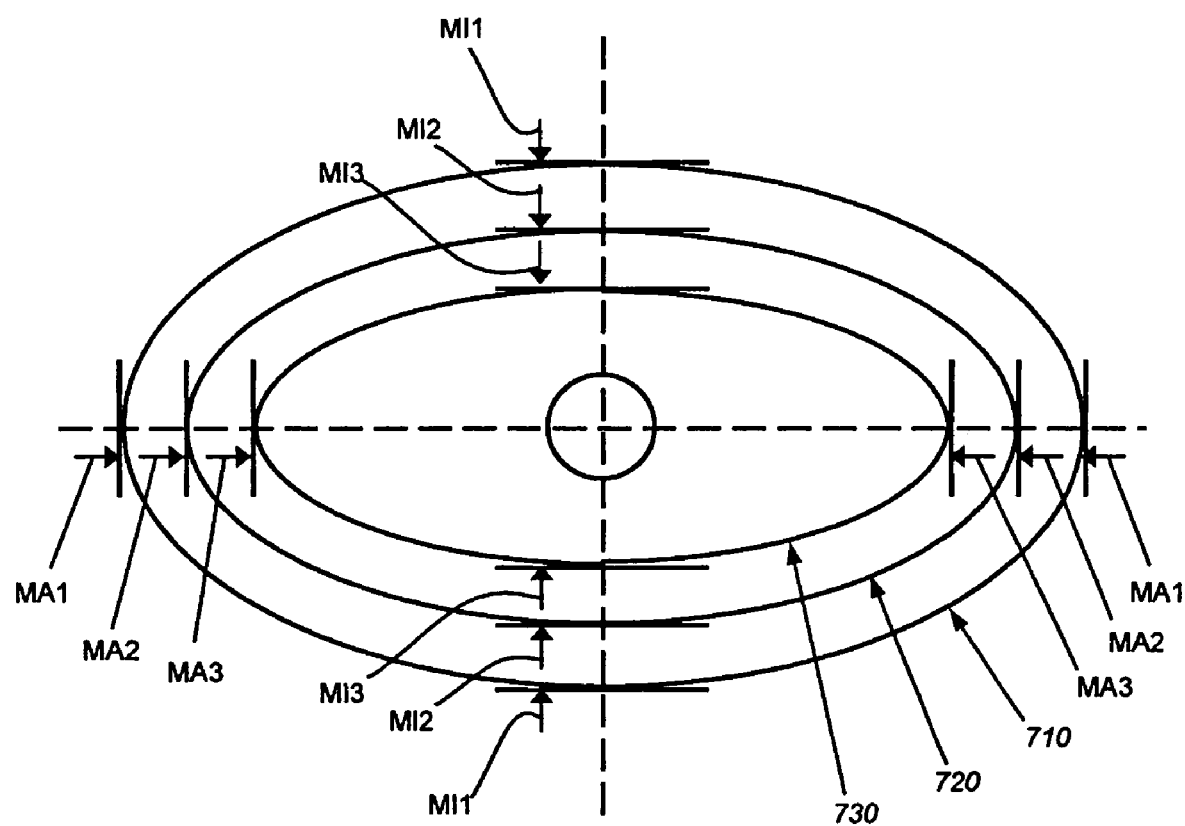
FIG. 10 is a simplified bottom view of the implant of FIG. 7 showing the relative dimensions of each tier.

As discussed, the drill assembly 100 forms a socket in the jawbone defined by a series of ovular, tiered holes that reduce in size from top to bottom. The implant 700 is sized to be pressed/tapped into the tiered socket with minimal clearance between the seated implant and surrounding material, thereby reducing the risk of failure and providing primary stability. The implant's exact dimension can be sized to accurately conform to the socket. In general, the implant's outer dimension is slightly larger than the surrounding hole to provided added holding strength and stability in a press fit. That is, where the drill points create non-uniform or compound-curved surfaces, the implant can be shaped to fill such surfaces. Hence the series of regular tiered ovals shown herein can, in fact be a more complex shape, particularly at the transition points between tiers. The approximate outer dimension of each tier is shown in FIG. 10. In one example, the upper tier 710 defines a major axis MA1 of approximately 8-9 millimeters and a minor axis MI1 of approximately 5-6 millimeters. The central tier 720 defines a major axis MA2 of approximately 6-7 millimeters and a minor axis MI2 of approximately 4-5 millimeters. The lowest tier 730 defines a major axis MA3 of approximately 5-6 millimeters and a minor axis MI3 of approximately 3-4 millimeters. These dimensions are highly variable depending upon the location and size of the replaced tooth. By way of example (see FIG. 8), the height H1 from the implant bottom 754 of the implant to the top of the upper tier 710 is approximately 10 millimeters. Likewise, the height H2 from the bottom to the top of the central tier 720 is approximately 8 millimeters, while the height from the bottom 754 to the top of the lowest tier 730 is approximately 6 millimeters. It, thus, follows that the pilot hole should extend at least 10 millimeters for the three-tiered implant 700 of this embodiment.

The number of tiers employed for the implant according to this invention is highly variable. In one embodiment, the number of tiers can be based upon the size and root depth of the replaced tooth. For example, where a tooth is somewhat smaller than maximum size, the implant can be sized to include only two tiers (having the approximate dimensions of the lowest 730 and central 720). A corresponding two-tiered socket is drilled by limiting the pilot hole to approximately 8 millimeters, rather than 10 millimeters (or full depth). For small teeth, an implant having only the lowest dimension tier (730) can be employed and the pilot hole depth is limited to approximately 6 millimeters. Note that the implant can include additional tiers as appropriate. Likewise, since the opposing lateral drill points in a set/pair may be sized or shaped differently from one another, any tier the socket, and the corresponding implant, can define a shape that is irregular, thereby allowing it to even more closely conform to the size and shape of the original replaced tooth's socket. In an embodiment, where a portion of the pilot hole remains in the socket bottom, the bottom 754 of the implant (regardless of number of tiers) can include a hole (790, shown in phantom in FIG. 7) through which a fastener (not shown) can pass into the pilot hole to further secure the implant. Alternatively, the pilot hole bottom can be filled with a structure that projects from the bottom of the implant to provide another narrow tier.

In addition, while a multi-tiered drill assembly is shown and described herein, it is expressly contemplated that a drill assembly with only one tier, or two, or more than three can be provided in alternate embodiments. In one exemplary procedure, a plurality of drill assemblies are each successively inserted into the pilot hole, each drill having lateral drill points the proper size and shape for forming a given tier in the overall socket. The terms "drill assembly" and "lateral drill points" should be taken broadly to define a mechanism containing one or more sets of opposed laterally extended drill points that dig out a socket having a generally non-circular shape. Likewise, while a bevel gear structure is employed to translate vertically aligned rotation from a conventional hand piece into lateral rotation, a specialized hand piece that imparts lateral rotation directly to the is drill assembly is expressly contemplated in alternate embodiments. Thus such a drill assembly may omit the upper portion bevel gear structure.

Figure 11:
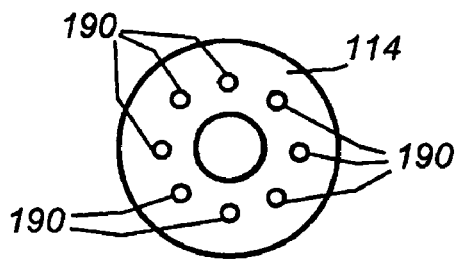
FIG. 11 is a top view of the indexing head of the drill in accordance with an illustrative embodiment.

Because the drill assembly forms a highly directional hole and entry of an elongated hand piece into the patient's mouth can only occur at a relatively limited range of angles, it is desirable to provide a mechanism that enables the relative angle of the drill assembly with respect to the hand piece (about the vertical axis) to be varied. This is accomplished using the above-described indexing head 114, shown further in FIG. 11. The indexing head includes a set of equally, circumferentially spaced holes. Spacing need not be equal in alternate embodiments, but adapted particularly to the most-comfortable entry angles for the practitioner. In this embodiment, there are eight holes. Allowing two crossing positions and two 45-degree intermediate positions therebetween (see FIG. 15).

Figure 12:
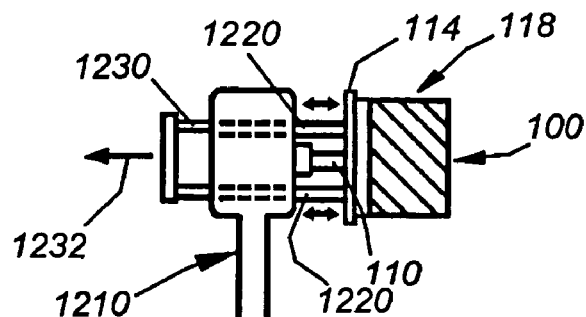
FIG. 12 is a side view showing the engagement of integral locking pins on a hand piece with the indexing head in accordance with an embodiment of this invention.

The indexing head is locked rotationally with respect to the hand piece using one or more locking pins. As shown in the embodiment of FIG. 12, the hand piece 1210 is specially adapted to include an axially movable pair of locking pins 1220 riding on a common support 1230. Moving the support (arrow 1232) away from the indexing head disengages the ends of the pins 1220 from their respective holes 190, and allows rotation to another rotational position about the drive axle 110. When the holes and pins are realigned in the desired positions, the pins are moved manually or under spring force back into engagement with the holes.

Figure 13:
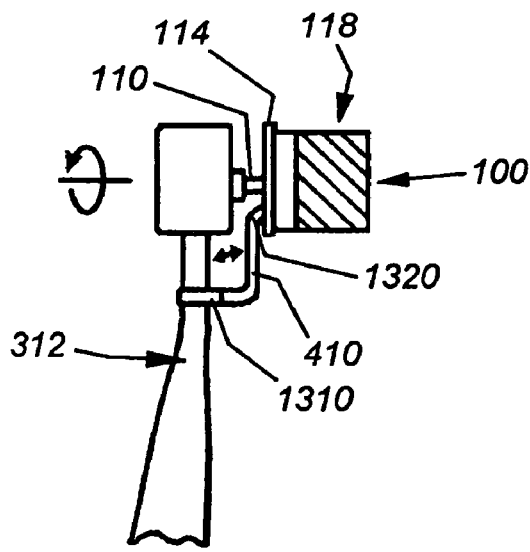
FIG. 13 is a side view showing the engagement of a retrofit locking pin assembly on a hand piece with the indexing head in accordance with an alternate embodiment of this invention.
Figure 14:
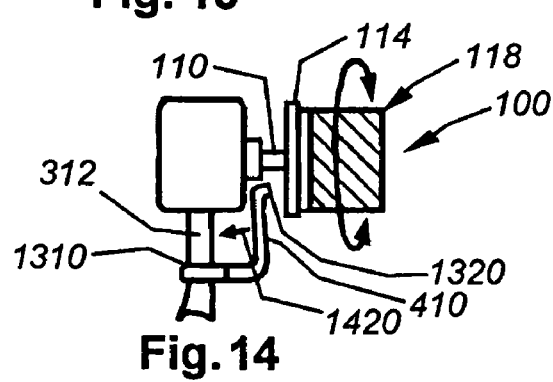
FIG. 14 is a side view showing the operation of the locking pin of FIG. 13 to allow rotation of the indexing head.

Alternatively, as shown in FIGS. 13 and 14 and described above, a locking assembly 410 can be retrofit (via a loop or collar 1310 about the hand piece shaft) to the hand piece 312. This locking assembly is constructed from spring material or with appropriate spring linkages that should be within the scope of those of ordinary skill. The tip 1320 of the locking assembly 410 is forcibly engaged with one of the indexing holes 190 as shown in FIG. 13. By applying withdrawal force (arrow 1420 in FIG. 14) the tip 1320 is disengaged from the hole 190, allowing the entire drill assembly to rotate about the axle 110 into the desired rotational orientation. When the desired rotational orientation is achieved, the tip is allowed to springingly re-engage the new hole 190, thereby rotationally locking the drill assembly with respect to the hand piece 312.

Figure 15:
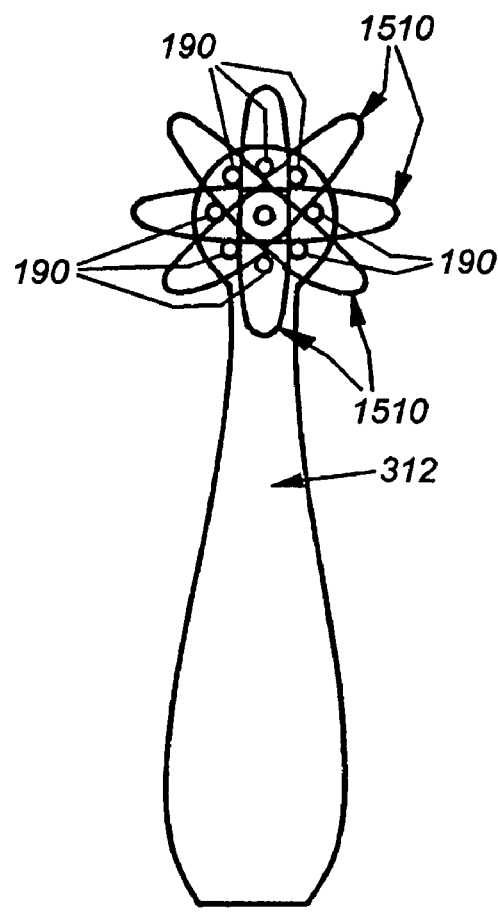
FIG. 15 is a top view of the hand piece with drill attached showing exemplary indexing positions.

As shown in FIG. 15, the simple arrangement of indexing holes 190 enables the illustrated multiplicity of rotational positions 1510 for the drill assembly. Note, however, that a variety of "locking assemblies" that allow the drill assembly to be permanently or variably positioned and locked against rotation with respect to the hand piece are expressly contemplated.

Figure 16:
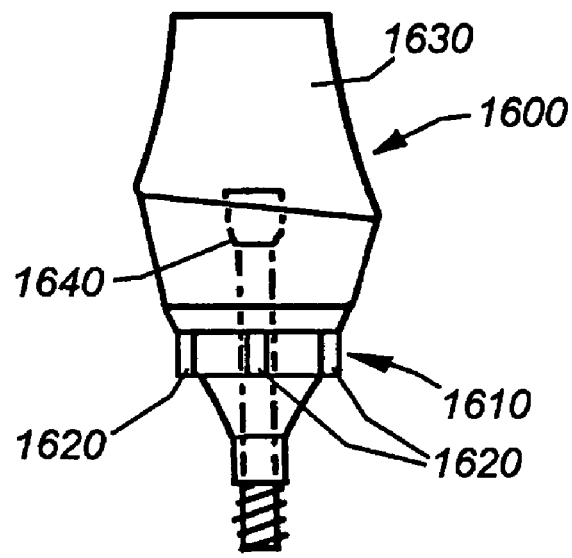
FIG. 16 is a partially exposed side view of a titanium abutment for use with the implant fixture in accordance with an illustrative embodiment.

Finally, as described generally above, the implant fixture 700 is adapted to receive an abutment onto which a crown or bridge is applied. A variety of abutment types can be employed with the implant fixture of this invention. By way of example, FIG. 16 details an embodiment of an adaptation of a so-called "prefabricated" abutment 1600 in which the entire structure is constructed from titanium. The abutment includes a lower base 1610 having appropriately sized and positioned wedges 1620 to be received by the notches 780 in the implant well 762 (see FIG. 7). The upper end 1630 of the abutment 1600 is adapted to receive a conforming crown or bridge. A screw 1640 passes through a hole in the center of the upper portion and out through the fixture. The screw engages the threaded hole in the center of the implant according to this embodiment.

Figure 17:
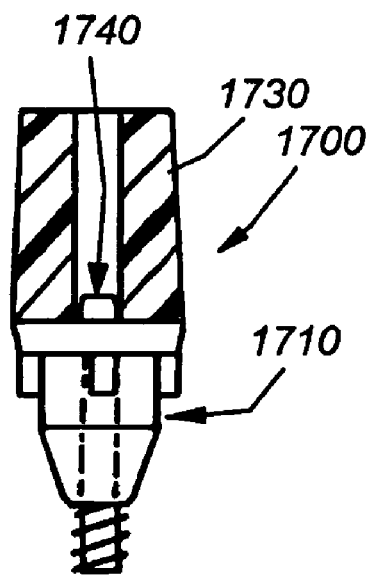
FIG. 17 is a side cross section of a composite plastic and titanium abutment for use with the implant fixture in accordance with an illustrative embodiment.

Briefly, FIG. 17 details another type of abutment 1700 that can be used with the implant according to this embodiment. This so-called "UCLA" or custom type abutment has a titanium fixture 1710 that conforms to the implant well. It has a plastic upper portion 1730 through which the fastening screw 1740 passes.

Figure 18:
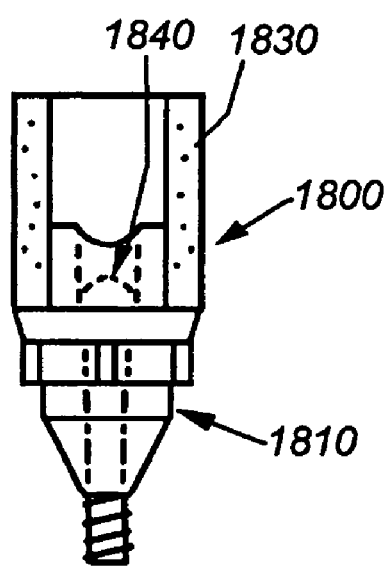
FIG. 18 is a side cross section of a composite ceramic and titanium abutment for use with the implant fixture in accordance with an illustrative embodiment.

The implant can also receive a so-called "porcelain" type abutment 1800, shown in FIG. 18. The fixture is titanium and shaped as described above. The upper portion 1830 is constructed from a ceramic, such as porcelain. The fastening screw 1840 passes through the upper portion and fixture, and into the implant. Note that the screw may have a lower tip (not shown) that is adapted to pass out through the bottom of the implant and into the jawbone (e.g. through the pilot hole). Again, the shape and configuration of the fixtures of abutments described herein, and the shape/configuration of the conforming implant well are highly variable.

It should be noted again that the ovoid socket shape generated by the opposed half-ovoid drill tips of this invention is only one of a large range of possible socket shapes generated by the lateral-axis drill of this invention. In alternate embodiments, the tips can define a variety of cross section shapes that form other anatomical shapes that can be used advantageously to fit implants and other appliances into bone and other materials.

The foregoing has been a detailed description of illustrative embodiments of the invention. Various modifications and additions can be made without departing from the spirit and scope thereof. For example, the materials described herein are not exhaustive, and any acceptable material can be employed for any component of this described system and method. Further, while a separate pilot hole is provided prior to formation of the socket, it is contemplated that the drill assembly can be modified to simultaneously drill a pilot hole using an appropriate vertically-oriented drill bit. Alternatively, a pilot hole may be omitted in certain embodiments. Also, while a conventional hand piece is employed, it is contemplated that a variety of additional attachments, guides and automated mechanisms can be employed to improve the accuracy and ease of socket formation. In addition, while terms of orientation, such as "vertical," "downward," "upper," "lower," "bottom," "transverse," "lateral," and the like are employed to describe various directions and positions in the environment of a jaw and with respect to the drill assembly, these terms should be taken as conventions only of relative orientation and direction and not as absolute conventions with respect gravity or fixed reference point. Accordingly, this description is meant to be taken only by way of example, and not to otherwise limit the scope of the invention.

What is claimed is:

1. A drill assembly for forming a dental implant socket in a jawbone comprising:
   a first pair of opposed drill points that rotate laterally along a first axis substantially transverse to a vertical axis taken along a direction of drilling into the jawbone, each drill point having a drill tip, and the two drill tips of the first pair of opposed drill points defining therebetween a maximum width;
   a framework that supports the first pair of drill points, the framework including a mounting that engages a hand piece; and
   a second pair of opposed drill points that rotate laterally along a second axis substantially transverse to the vertical axis and substantially parallel to the first axis, the second pair of opposed drill points supported by the framework and located further from the mounting along the framework than the first pair of opposed drill points, each drill point having a drill tip, and the two drill tips of the second pair of opposed drill points defining therebetween a maximum width, wherein
   the maximum width of the first pair of opposed drill points is greater than the maximum width of the second pair of opposed drill points.

2. The drill assembly as set forth in claim 1 wherein the mounting includes an axle that engages the hand piece and a gear assembly that transmits rotation about the vertical axis into rotation about first axis.

3. The drill assembly as set forth in claim 1 wherein each of the opposed drill points comprises a half of an ovoid shape.

4. The drill assembly as set forth in claim 1 further comprising a third pair pct of opposed drill points that rotate laterally along a third axis substantially transverse to the vertical axis, the third pair of opposed drill points being located further from the mounting along the framework than the second pair of opposed drill points, each drill point of the third pair of opposed drill points having a drill tip, and the two drill tips of the third pair defining therebetween a maximum width, wherein the maximum width of the third pair of drill points is less than the maximum width of the second pair of drill points.

5. The drill assembly as set forth in claim 4 wherein each of the first pair of opposed drill points, the second pair of opposed drill points and the third pair of opposed drill points include a respective first axle and first gear, second axle and second gear and third axle and third gear each operatively connected together along the framework.

6. The drill assembly as set forth in claim 1 wherein the mounting includes an indexing head constructed and arranged to allow the mounting to be rotated into a plurality of orientations with respect to the hand piece.

7. The drill assembly as set forth in claim 6 wherein the indexing head includes a plurality of indexing holes that are each removably engaged by a locking pin operatively connected to the hand piece.

8. The drill assembly as set forth in claim 1 wherein the framework includes, at a side along the vertical axis opposite the mounting, a stop tip adapted to ride to the bottom of a pilot hole in the jawbone.

9. A drill assembly for forming a dental implant socket in a jawbone, the drill assembly comprising:
   a fixture configured for connection to a hand piece;
   a first pair of opposed drill points adapted to rotate about a first axis, the first axis about which the first pair of opposed drill points rotates is orthogonal to a direction of drilling into the jawbone;
   a second pair of opposed drill points adapted to rotate about a second axis that is parallel to the first axis and spaced from the first axis along the direction of drilling into the jawbone and;
   at least one transmission element connecting the fixture to the first pair of opposed drill points
   wherein
   the first pair of drill points has a maximum width,
   the second pair of drill points has a maximum width, and
   the maximum width of the second pair of drill points is less than the maximum width of the first pair of drill points.

10. The drill assembly of claim 9 wherein each pair of opposed drill points has either a half ovoid shape or a conical shape.

11. The drill assembly of claim 10 wherein the second pair of drill points counter-rotate relative to the first pair of drill points.

12. The drill assembly of claim 9 wherein the fixture includes a drive shaft configured for rotation by the hand piece.

13. The drill assembly of claim 10 further comprising:
a framework that supports the first pair of drill points and the at least one transmission element; and
a tip attached to the framework, wherein the tip is adapted to be received in a pilot hole formed in the jawbone.

14. The drill assembly of claim 9 wherein the at least one transmission element is a gear.

15. The drill assembly of claim 9 wherein the hand piece has a longitudinal axis, and the drill assembly further comprises means for adjusting the longitudinal axis of the hand piece relative to the first axis about which the first pair of drill points rotate.

16. A drill assembly for forming a dental implant socket in a jawbone, the drill assembly comprising:
a fixture configured for connection to a hand piece;
a first pair of opposed drill points adapted for rotation about one or more first axes that are each orthogonal to a direction of drilling into the jawbone, the first pair of opposed drill points defining a maximum width;
a second pair of opposed drill points adapted for rotation about one or more second axes, wherein the one or more second axes are each parallel to and spaced from the one or more first axes along the direction of drilling into the jawbone, the second pair of opposed drill points defining a maximum width and;
at least one transmission element connecting the fixture to the first pair of opposed drill points
wherein
the maximum width of the first pair of opposed drill points is greater than the maximum width of the second pair of opposed drill points such that the dental implant socket formed by the drill assembly has a series of tapering tiers.

17. The drill assembly of claim 16 wherein each drill point has either a half ovoid shape or a conical shape.

* * * * *

UNITED STATES PATENT AND TRADEMARK OFFICE
CERTIFICATE OF CORRECTION

PATENT NO. : 7,695,280 B1
APPLICATION NO. : 11/305250
DATED : April 13, 2010
INVENTOR(S) : Ernest M. Yazigi et al.

It is certified that error appears in the above-identified patent and that said Letters Patent is hereby corrected as shown below:

In the Specification

Col. 2, line 30 should read: "points can ~~is~~ be adapted to counter-rotate with respect to"

Col. 2, line 63 should read: "bottom tier of drill points engages the jawbone ~~to~~ material;"

Col. 5, line 26 should read: "When the ~~to~~ shaft 110 is chucked in the hand piece 312, the"

Col. 8, line 3 should read: "imparts lateral rotation directly to the ~~is~~ drill assembly is"

Signed and Sealed this
Tenth Day of September, 2013

Teresa Stanek Rea
*Acting Director of the United States Patent and Trademark Office*